United States Patent [19]
Marks et al.

[11] Patent Number: 5,300,598
[45] Date of Patent: Apr. 5, 1994

[54] METHOD OF POLYMERIZING EXO-METHYLENE CYCLIC ORGANIC COMPOUNDS USING HOMOGENEOUS RING-OPENING CATALYSTS

[75] Inventors: Tobin J. Marks, Evanston; Xinmin Yang, Chicago; Li Jia, Evanston, all of Ill.

[73] Assignee: Northwestern University, Evanston, Ill.

[21] Appl. No.: 962,390

[22] Filed: Oct. 16, 1992

[51] Int. Cl.$^5$ .................... C03G 61/06; C08F 4/64
[52] U.S. Cl. ................... 526/134; 526/160; 526/170; 526/308
[58] Field of Search ........... 526/132, 134, 160, 308, 526/170, 282

[56] References Cited

PUBLICATIONS

Pinazzi, et al., "Polymerization of Methylenecyclobutane, Synthesis of an Isopolyisoprene," Die Makromolekulare Chemie 122 (1969), pp. 105-122.

Takemoto, et al., "Vinylpolymerisation," Die Makromolekulare Chemie 109 (1967), pp. 81-86.

Rossi, et al., "On the Ring-Opening Polymerization of Methylenecyclobutane," Macromolecules, vol. 5, No. 3, (1972), pp. 247-249.

Pinazzi, et al., "Polymerisation du methyleneyclobutane Obtention de l'isocaoutchouc," Die Makromolekulare Chemie 147 (1971), pp. 15-33.

Hiraguri, et al., "Radical Polymerization of 3-Substituted-1-Methylenecyclobutanes," Journal of Polymer Science, vol. 26 (1988), pp. 381-384.

*Primary Examiner*—Fred Teskin
*Attorney, Agent, or Firm*—Welsh & Katz, Ltd.

[57] ABSTRACT

The regiospecific $(1,2\text{-Me}_2\text{C}_5\text{H}_3)_2\text{ZrMe}^+\text{-MeB}(\text{C}_6\text{F}_5)_3^-$ mediated ring-opening polymerization of methylenecyclobutane and its copolymerization with ethylene to polyolefins of microstructure—$\{CH_2CH_2CH_2C(CH_2)\}-_n$ and $\{-[CH_2CHR]-_x[CH_2CH_2CH_2C(CH_2)]-_y\}_n$ respectively, is disclosed.

10 Claims, No Drawings

METHOD OF POLYMERIZING EXO-METHYLENE CYCLIC ORGANIC COMPOUNDS USING HOMOGENEOUS RING-OPENING CATALYSTS

BACKGROUND OF THE INVENTION

This invention was made with Government support under the Department of Energy Office (Contract DE-FG02-86ERI3511/5). The Government has certain rights under this invention.

This application relates to catalysts and more particularly to homogeneous catalysts for use in polymerization via the ring opening of strained ring systems.

In the presence of Ziegler-Natta catalysts, methylenecyclobutane A can be polymerized into a polymer consisting of a mixture of micro-structure units B and C, through a ring-opening mechanism and a simple vinyl type insertion mechanism, respectively.

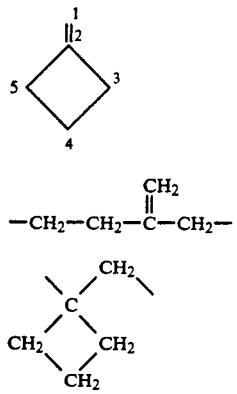

Micro-structure B is particularly interesting in that it not only represents the thermodynamically unstable form of the synthetic rubber poly(isoprene), but when incorporated into copolymers with simple olefins, it can impart useful functionalities. Although it has been shown that several Ziegler-Natta catalysts including AlEt$_2$Cl-Cr(acac)$_3$-TiCl$_4$ARA can selectively produce a polymer with structure B dominating, the activity of these catalysts appears extremely sluggish. More importantly, the mechanism of the ring-opening process which was earlier proposed to involve the oxidative addition of the ring C—C bond seems unlikely with the early transition metals where the required oxidation states may not necessarily be available.

SUMMARY OF THE INVENTION

Therefore, an object of the subject invention is a novel catalyst for polymerizations having a high activity.

A further object of the subject invention is a catalyst for olefin polymerization which operates via a ring-opening mechanism.

A still further object of the subject invention is a catalyst by which electrophilic metallocene cations catalyze the facile regioselective ring-opening homopolymerization of exo-methylene substituted cyclic organic compounds and the copolymerization of such compounds with α-olefins such as ethylene, propylene, butylene and styrene via a β-alkyl shift mechanism.

Catalysts having RB(C$_6$F$_5$)$_3^-$, B(C$_6$F$_5$)$_4^-$ methylalumoxane derivatives as the charge-compensating anion, especially Cp$_2$ZrMe+MeB(C$_6$F$_5$)$_3^-$(Cp=-η$^5$—1,2-Me$_2$C$_5$H$_3$), can catalyze the ring-opening polymerization of methylenecyclobutane to form the iso-rubber micro-structure B with not only very high selectivity, but also great efficiency. Such catalysts also catalyze the co-polymerization of simple olefins with ex-omethylene cyclic organic monomers, such as methylenecyclobutane. Polyolefins of the structure [CH$_2$CH$_2$CH$_2$C(CH$_2$)]$_n$ and ([CH$_2$CHR]$_x$[CH$_2$CH$_2$CH$_2$C(CH$_2$)]$_y$)$_n$ can thus be prepared where R = an alkyl or aryl group. The probable mechanism of the methylenecyclobutane polymerization is shown in the Reaction Sequence I.

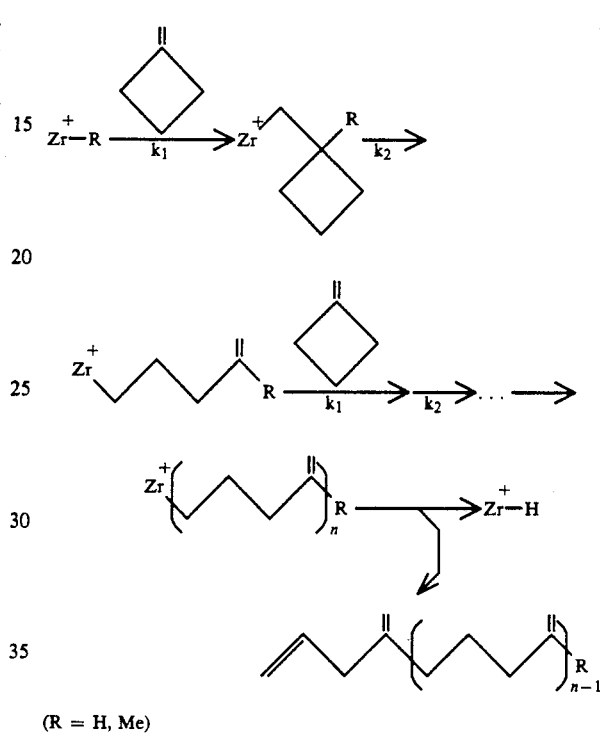

(R = H, Me)

The key step is a heretofore unrecognized ring opening polymerization β-alkyl shift. Such a polymerization process should be applicable to the polymerization of a variety of strained ring monomers having exocyclic unsaturation.

DETAILED DESCRIPTION OF THE INVENTION

Facile β-alkyl transpositions are a distinctive feature of electrophilic d$^0$f$^n$ hydrocarbyl chemistry (e.g., equation (II)) and

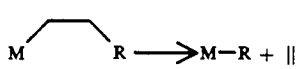

represent an important chain transfer channel in certain olefin polymerization processes. In principle, such transpositions might also provide an unusual pathway to functionalized polyolefins by coupling olefin insertion and strained monomer ring-opening sequences (equation (III)).

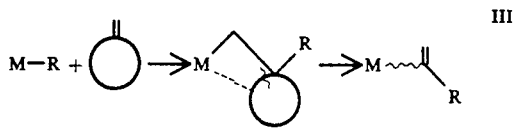

In the presence of conventional heterogeneous Ziegler-Natta catalysts, methylenecyclobutane A undergoes a sluggish reaction to afford polymers having ring-opening or mixed ring-opening/insertion-derived microstructures (B,C). The ring-opened structures w ®r ®ascribed to oxidative addition at the C3-C4/C4-C5 junctures of A. As stated above, the subject invention involves electrophilic zirconocene cations, which catalyze the facile, regioselective ring-opening homopolymerization of exo-methylene cyclic organic compounds and copolymerization with ethylene via a β-alkyl shift mechanism.

The exo-methylene cyclic organic compounds generally may be represented by the formula:

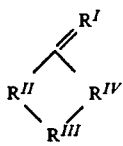

where $R^I$, $R^{II}$, $R^{III}$ and $R^{IV}$ are organic fragments which may include O, N, S or P. Preferably, the monomer is methylenecyclobutane.

In general, reaction of the catalyst $Cp_nMR^+_{3-n}B(D_6F_5)_3R'$[31], where Cp is a cyclopentadienyl containing ligand where n=1 or 2, M=Ti, Zr, or Hf, and R, R' is an alkyl (C=1-5), hydride, or aryl, with A proceeds rapidly in toluene solution to yield, after work-up, polymethylenecyclobutane (PMCB, Table I). Examples of viable catalysts are $(C_5H_5)_2ZrMe^+MeB(C_6F_5)_3^-$ and (1, 2 $Me_2C_5H_3)_2$ $ZrMe^+MeB(C_6F_5)_3^-$, or $(C_5H_5)_2ZrR_2$ and methylalumoxane, (R=alkyl, aryl, hydride, halide or alkoxide. Other nonpolar solvents, both aliphatic (C=1-12) and aromatic (C=6-20) as well as others may be used. $^1H$ and $^{13}C$ NMR spectra reveal that the polymer microstructure is almost exclusively B (≧95%; minor traces of C may be present), indicating that the present polymerization is highly selective for the ring-opening pathway. The length of reaction time/extent of conversion appears to have no detectable effect on selectivity (Table I, entries 1, 2). However, lower reaction temperatures appear to slightly favor microstructure C (Table I, entry 3 by $^1H$ NMR). NMR analysis also indicates allylic end groups in all of those PMCB samples, consistent with chain transfer via β-H elimination. The present PMCB samples are soluble in aromatic solvents, but insoluble in $CHCl_3$ or acetone.

Copolymerization of A with α-olefins such as ethylene can be readily effected by stirring A neat or in toluene solution with 1 under 1.0 atm of ethylene (Table I, entries 4–6). $^1H$ and $^{13}C$ NMR spectroscopy indicates

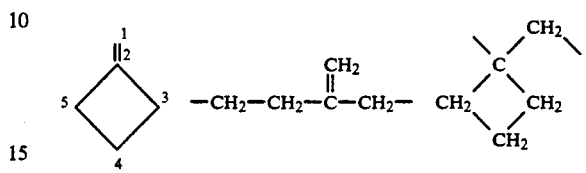

that the derived copolymers have ring-opened microstructure D exclusively and that the x and y $$([CH_2CHR]_x [CH_2CH_2CH_2C(CH_2)]_y)_n \quad D$$

proportions can be controlled via the reaction stoichiometry.

TABLE I

Polymerization of Methylenecyclobutane and Copolymerization with Ethylene Using $(1,2-Me_2C_5H_3)_2ZrMe^+MeB(C_6F_5)_3^-$ as a Catalyst

| Entry | Catalyst Amount (μmol) | Methylene cyclobutane Amount (mmol) | Ethylene Pressure (1 atm) | Solvent (mL) | Temp (°C.) | Reaction Time (h) | Yield of Polymer (g) | /=)[b] | $M_w(M_o)^c$ × 1000 |
|---|---|---|---|---|---|---|---|---|---|
| 1 | 7.33 | 27.0 | 0.0 | Toluene (10) | 20 | 16 | 1.7 (100%)[a] | — | 83.3 (38.5) |
| 2 | 7.33 | 27.0 | 0.0 | Toluene (10) | 20 | 5 | 1.1 (60%)[a] | — | n.a. |
| 3 | 7.33 | 23.8 | 0.0 | Toluene (10) | −30 | 20 | 0.16 (9%)[a] | — | n.a. |
| 4 | 7.33 | 23.8 | 1.0 | None | 20 | 0.17 | 0.84 | 0.81 | 89.9 (35.5) |
| 5 | 7.33 | 8.3 | 1.0 | Toluene (15) | 20 | 0.17 | 0.98 | 0.21 | 255.3 (192.0) |
| 6 | 7.57 | 1.2 | 1.0 | Toluene | 20 | 0.12 | 0.60 | ca. 0.002 | n.a. |

[a]Monomer conversion by $^1H$ NMR.
[b]Ratio of methylenecyclobutane and ethylene incorporated into the copolymer as determined by $^1H$ NMR.
[c]By GPC versus polystyrene.

All operations were performed with rigorous exclusion of oxygen and moisture in flamed Schlenk-type glassware in a dual manifold Schlenk line or interfaced to a high vacuum ($10^{-5}$ torr) system, or in a nitrogen or argon filled glovebox with a high capacity atmosphere recirculator. Argon, ethylene and propylene were purified by passage through a supported MnO oxygen removal column and a molecular sieve column. Aliphatic hydrocarbon solvents were pretreated with concentrated $H_2SO_4$, $KMnO_4$ solution, $MgSO_4$ and Na, 4A molecular sieves. All reaction solvents were distilled from Na/K/benzophenone under nitrogen and were condensed and stored in vacuo in bulbs on the vacuum line containing a small amount of $[Ti(\eta^5-C_5H_5)_2Cl]_2ZnCl_2$ as indicator. Methylenecyclobutane was additionally dried over Na/K.

EXAMPLES

Preparation of Catalyst

Synthesis of $Cp_2ZrMe^+MeB(C_6F_5)_3^-$
$(Cp''=1,2Me_2C_5H_3)$ $Cp_2ZrMe_2$ (0.116 g, 0.378 mmol) and $B(C_6F_5)_3$ (0.194 g, 0.379 mmol) were loaded into a 25 mL flask. Benzene (10 mL) was then vacuum transferred into this flask at $-78°$ C., as the mixture was slowly warmed to ambient temperature. A clear solution was first seen but it quickly became cloudy as solids began to precipitate. After stirring for 2.5 h, the mixture was filtered. The light yellow solid was washed once with a small amount of benzene and dried under vacuum. Yield, 65%.

Synthesis of
$Cp_2ZrCH_3^+CH_3B(C_6F_5)_3^-(Cp=\eta^5-C_5H_5)$ $Cp_2ZrMe_2$ (0.100 g, 0.398 mmol) and $B(C_6F_5)_3$ (0.205 g, 0.400 mol) were loaded into a 25 mL flask in the glovebox. Benzene (15 mL) was then vacuum-transferred into this flask at $-78°$ C. The mixture was slowly warmed to room temperature and stirred for 1.5 h. At this time large quantities of solid precipitated. Pentane (10 mL) was vacuum-transferred into the flask and the mixture was filtered after stirring. The light yellow solid was washed once with 5 mL of pentane and dried under vacuum. Yield, 72%.

Alternately, $Cp_2ZrMe_2$ (0.264 g, 1.052 mmol) and $B(C_6F_5)_3$ (0.539 g, 1.055 mmol) may be stirred in 20 mL of pentane in a 50 mL flask for 12 h at room temperature. The mixture is filtered and the solid washed once with pentane and dried under vacuum. Yield, 81%.

EXAMPLE 1

Homo-polymerization of Methylenecyclobutane $(1,2-Me_2C_5H_3)_2ZrMe^+MeB(C_6F_5)_3^-$ (6 mg) was loaded into a 25 mL flask in a glovebox. Toluene (10 mL) and methylenecyclobutane (2.4 mL) were vacuum-transferred into the above flask at $-78°$ C. The flask was backfilled with Ar and the solution stirred at room temperature for 16 h. The reation was then quenched with methanol. After removing the volatiles under vacuum, the elastomeric polymeric product was washed several times with toluene and dried under vacuum. Yield 1.73 g. The polymer was characterized by $^1H$ and $^{13}C$ NMR spectroscopy. The $^1H$ NMR also gives an number-averaged molecular weight ($M_n$) of ca.2,000.

EXAMPLE 2

Co-polymerization of Methylenecyclobutane with Ethylene $(1,2-Me_2C_5H_3)_2ZrMe^+MeB(C_6F_5)_3^-$ (6 mg) was loaded into a 25 mL flask in a glovebox. Toluene (10 mL) and methylene-cyclobutane (0.70 mL) were vacuum-transferred into the above flask at $-78°$ C. The solution was stirred at room temperature under 1 atm of ethylene for 10 min. The reaction was then quenched with methanol. The white solid product was collected by washing with acetone and drying under vacuum. Yield 0.98 g. NMR (toluene-$d_8$, 90° C.): $^1H$ : $\delta$ (PPM) 4.83, 2.06, 1.65, 1.50, 1.35. $^{13}C$: $\delta$ (ppm) 150.2, 149.9, 109.5, 109.3, 36.9, 36.4, 30.16, 27 28.4B, 26.78.

EXAMPLE 3

Co-polymerization of Methylenecyclobutane with Ethylene $(1,2-Me_2C_5H_3)_2ZrMe^+MeB(C_6F_5)_3^-$ (6.2 mg) was loaded into a 25 mL flask in the glovebox. Toluene (25 mL) and methylene-cyclobutane (0.10 mL) were vacuum-transferred into the above flask at $-78°$ C. The solution was stirred at room temperature under 1 atm of ethylene for 7.0 min. The reaction was then quenched with methanol. The white solid product was collected by washing with acetone and drying under vacuum. Yield 0.60 g.

EXAMPLE 4

Co-polymerization of Methylenecyclobutane with Ethylene $(1,2-Me_2C_5H_3)_2ZrMe^+MeB(C_6F_5)_3^-$ (6 mg) was loaded into a 25 mL flask in the glovebox. Methylenecyclobutane (2.0 mL) was vacuum-transferred into the above flask at $-78°$ C. The solution was stirred at room temperature under 1 atm of ethylene for 10 min. The reaction was then quenched with methanol. The product was collected by washing with acetone and drying under vacuum. Yield 0.84 g.

EXAMPLE 5

Co-polymerization of Methylenecyclobutane with Ethylene $(C_5H_5)_2ZrMe^+MeB(C_6F_5)_3^-$ (25.8 mg) was loaded into a 25 mL flask in the glovebox. Toluene (25 mL) and methylenecyclobutane (0.10 mL) were vacuum-transferred into the above flask at $-78°$ C. The solution was stirred at room temperature under 1 atm of ethylene for 2.0 min. The reaction was then quenched with methanol. The white solid product was collected by washing with acetone and drying under vacuum. Yield 0.68 g.

With regard to the polymerization mechanism, it seems unlikely, based upon known chemistry, that methylenecyclobutane can support two-electron (or one-electron) oxidative addition-reductive elimination propagation sequences. Furthermore, $^1H$ and $^{13}C$ NMR analysis of copolymerizations with $^{13}CH_2=^{13}CH_2$ indicates the presence of one $^{13}$-$CH_2$- unit adjacent to every exomethylene group, compatible only with a $C_2$-$C_3$/-$C_2$-$C_5$ ring opening. Combined with prior evidence for $\beta$-Me shifts in propylene polymerizations at cationic zirconocene centers and $\beta$-alkyl shift-based methylenecyclobutane $-->1,4$-pentadiene rearrangements at isoelectronic scandocene centers, the pathways of Reaction Sequence I set forth above seem most compatible with the present results. Additionally, kinetic measurements ([1]=1.57-15.7 mm [A]= 1.05-2.09M) reveal that the homopolymerization of A obeys rate law (IV), where $$-\frac{d[A]}{dt} = k\{1\}^2[A]^2 \qquad \text{IV}$$

$K=4.1$ (1)$\times 10^{-2}M^{-1}S^{-1}$ at $-5.5°$ C. Thus, the turnover-limiting step under these conditions appears to be olefin insertion rather than cyclobutane ring opening. As a result, it would appear that $\beta$-alkyl shift processes represent an efficient propagation pathway for the synthesis of new exo-methylene-functionalized polyolefins.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

We claim:

1. A method for the ring-opening copolymerization of an exomethylene substituted cyclic organic compound with one or more $\alpha$-olefin comprising the steps of adding a solvent and an exo-methylene cyclic organic compound at a temperature of about $-78°$ C. to a flask containing a catalyst, said catalyst including an electrophilic methallocene cation, adding an $\alpha$-olefin, stirring, quenching and recovering the polymer product.

2. The method of claim 1 wherein said solvent is a nonpolar organic solvent.

3. The method of claim 2 wherein said solvent is selected from the group consisting of aliphatic and aromatic hydrocarbons.

4. The method of claim 2 wherein said solvent is toluene.

5. The method of claim 1 wherein said exomethylene cyclic organic compound is methylenecyclobutane.

6. The method of claim 1 wherein said catalyst comprises $L_nMR^+_{3-n}B(C_6F_5)_3R'^-$, where $L_n=$a cyclopentadienyl-containing ligand (n=1 or 2), M=Ti,Zr, Hf, and R=R'=alkyl, aryl, hydride or $-C_6F_5$ group.

7. The method of claim 1 wherein said $\alpha$-olefin is ethylene, propylene, butylene or styrene.

8. The method of claim 3, wherein said catalyst is prepared from $L_nMR_{3-n}$ and methyl alumoxane where M=Ti,Zn,Hf, R=alkyl, aryl, hydride, alkoxide or halide and $L_n=$a cyclopentadienyl-containing ligand (n=1,2).

9. A method for the polymerization of olefins comprising the steps of adding toluene and methylenecyclobutane at a temperature of about $-78°$ C. to a flask containing a catalyst of the formula $Cp_2ZrMe^+MeB(C_6F_5)_3^-$, stirring at 20° C. with an olefin, quenching with methanol and recovering the polymerized product, where Cp=a cyclopentadienyl-containing ligand.

10. The method of claim 1 wherein said catalyst is $(C_5H_5)_2ZrMe^+MeB(C_6F_5)_3^-$ or $(1,2\ Me_2C_5H_3)_2ZrMe^+MeB(C_6F_5)_3^-$.

* * * * *